US005285789A

United States Patent [19]

Chen et al.

[11] Patent Number: 5,285,789

[45] Date of Patent: Feb. 15, 1994

[54] ULTRASONIC TRANSDUCER APODIZATION USING ACOUSTIC BLOCKING LAYER

[75] Inventors: James N. C. Chen, Chelmsford, Mass.; Gregory G. Vogel, Londonderry, N.H.; Martin K. Mason, Andover, Mass.

[73] Assignee: Hewlett-Packard Company, Palo Alto, Calif.

[21] Appl. No.: 871,495

[22] Filed: Apr. 21, 1992

[51] Int. Cl.[5] .......... A61B 8/00

[52] U.S. Cl. .......... 128/662.03; 310/334

[58] Field of Search .......... 310/334-337; 128/662.03-662.04

[56] References Cited

U.S. PATENT DOCUMENTS

| | | | |
|---|---|---|---|
| 3,876,890 | 4/1975 | Brown et al. | 310/334 |
| 3,939,467 | 2/1976 | Cook et al. | 310/334 |
| 3,958,559 | 5/1976 | Glenn et al. | 128/2 |
| 4,248,090 | 2/1981 | Glenn | 73/620 |
| 4,425,525 | 1/1984 | Smith et al. | 310/334 |
| 4,460,841 | 7/1984 | Smith et al. | 310/334 |
| 4,556,814 | 12/1985 | Ito et al. | 310/334 |
| 4,700,575 | 10/1987 | Geithman et al. | 73/642 |
| 4,794,930 | 1/1989 | Machida et al. | 128/662.03 |

OTHER PUBLICATIONS

Harrison et al., "Single-Transducer Electrode Design for Beam Shaping in Biomedical Ultrasound," *IEEE Transactions on Ultrasonics, Ferroelectrics and Frequency Control*, vol. UFFC-33, No. 3, May 1986.

*Primary Examiner*—Francis Jaworski

[57] ABSTRACT

An ultrasound transducer for imaging a target features a piezoelectric transducer element for emitting an ultrasonic wave toward the target and an apodizer fashioned from a thin sheet acoustic blocking layer. The ultrasound acoustic blocking layer is placed between the front surface of the transducer and the target for substantially blocking the ultrasonic wave emission from a portion of the front surface area defining an inactive area. The blocking layer allows transmission of the ultrasonic emission from another portion of the front surface area defining an active area, and includes a thin sheet of polymer blocking material patterned for covering the inactive area of the front surface. The blocking material is attached to the front surface of the transducer element, embedded within an acoustic lens, or incorporated into an adapter which attaches to the body of the transducer. The thin sheet of blocking material is patterned as sawteeth aligned in opposite rows and pointing toward a midline of the transducer. The sawteeth are uniformly shaped and spaced, and positioned anti-symmetric, or the sawteeth are pseudo-randomly shaped and spaced. Alternatively, the thin sheet of blocking material is patterned as a grid of pseudo-randomly selected blocking areas.

24 Claims, 6 Drawing Sheets

ULTRASONIC TRANSDUCER APODIZATION USING ACOUSTIC BLOCKING LAYER

BACKGROUND OF THE INVENTION

This invention relates to improving the radiation pattern of ultrasonic transducers.

In recent years ultrasonic imaging techniques have become prevalent in clinical medical diagnosis. Such techniques have been utilized for some time in the fields of obstetrics, neurology, and cardiography. This technique has been used to measure and record the dimensions and position of deep lying organs and physiological structures throughout the body. A wide variety of ultrasound transducers and systems are used for imaging purposes. The systems range from a single crystal mechanically swept scanner, to linear arrays, to phased array sector scanners.

Phased array ultrasound imaging systems have gained wide acceptance as the primary method of ultrasound imaging, particularly due to an ability to electronically form, focus, and steer an ultrasound imaging beam in the imaging plane. Ideally, the result is a thin beam of ultrasound energy which can be steered in a lateral direction to provide an imaging plane. Typically, a plurality of parallel piezoelectric transducer elements are arranged as parallel columns along the lateral direction of the transducer to form a phased array transducer, with beamforming and steering control in the lateral direction. Controlling the ultrasound beamforming in the elevational plane is more difficult since typically there are no multiple transducer elements in the elevational direction with which to electronically focus the beam. An acoustic lens placed in front of the transducer is often used to obtain a single elevational focus for the generated ultrasound beam. However, diffraction due to the finite length of the transducer crystal in the elevational direction causes side lobes to appear in elevation which interfere with imaging by the main lobe.

Apodization, application of an acoustic amplitude weighted window across the transducer crystal in the elevational direction, has been shown to reduce the level of elevational side lobes. Apodization methods which have been used to control elevational side lobes include selectively poling the transducer crystal to modulate the polarization efficiency of the piezoelectric crystal in the elevational direction, and electrode shading in which an acoustic attenuative material of varying thickness is overlaid on the edge of the transducer crystal to attenuate the output of the crystal as a function of the material thickness.

SUMMARY OF THE INVENTION

The present invention provides an apodized ultrasound transducer which achieves improved elevational beamforming performance through the use of a thin sheet acoustic blocking layer. The transducer achieves apodized performance without the manufacturing costs typically associated with apodized transducers. The transducer featuring the thin sheet acoustic blocking layer of this invention is easy to manufacture, provides reproducible performance, and may be easily reconfigured during manufacturing by simply changing the thin sheet blocking pattern.

In one aspect of the invention an ultrasound transducer for imaging a target features a piezoelectric transducer element having a front surface for emitting an ultrasonic wave toward the target, and for receiving an echo of the emitted ultrasonic wave returned from the target. An ultrasound blocking means is placed between the front surface of the transducer and the target for substantially blocking the ultrasonic wave emission from a portion of the front surface area defining an inactive area. The blocking means allows transmission of the ultrasonic emission from another portion of the front surface area defining an active area. Preferably the transducer is a phased array transducer.

In preferred embodiments, the ultrasound blocking means includes a thin sheet of blocking material patterned for covering the inactive area of the front surface. The blocking material is a thin sheet polymer, such as TYVEK, having acoustic blocking attenuation of at least −40 dB at the ultrasonic wave frequency.

In other preferred embodiments the thin sheet of blocking material is attached to the front surface of the transducer element, or the thin sheet is embedded within an acoustic lens. The blocking material is also incorporated into an adapter which attaches to the body of the transducer.

In still other preferred embodiments, the thin sheet of blocking material is patterned as sawteeth aligned in opposite rows and pointing toward a midline of the transducer. The bases of adjacent sawteeth in each row are connected along an edge corresponding to opposite peripheral edges of the transducer front surface.

In yet other preferred embodiments the sawteeth in each row are uniformly shaped and spaced. The sawteeth of the one row are positioned anti-symmetric with respect to the sawteeth of the other row. The uniform spacing is less than 10 times the wavelength of the ultrasonic wave, and more preferably less than the wavelength of the ultrasonic wave. In other preferred embodiments the sawteeth are pseudo-randomly shaped and spaced, or the thin sheet of blocking material is patterned as a grid of pseudo-randomly selected blocking areas.

Thus, the invention described herein offers the advantages of providing a low cost apodized ultrasound transducer having improved performance over conventional transducers, while providing ease of manufacturability and configuration.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being place upon illustrating the principles of the invention.

DETAILED DESCRIPTION OF THE PREFERRED EMBODIMENT

Figure 1:
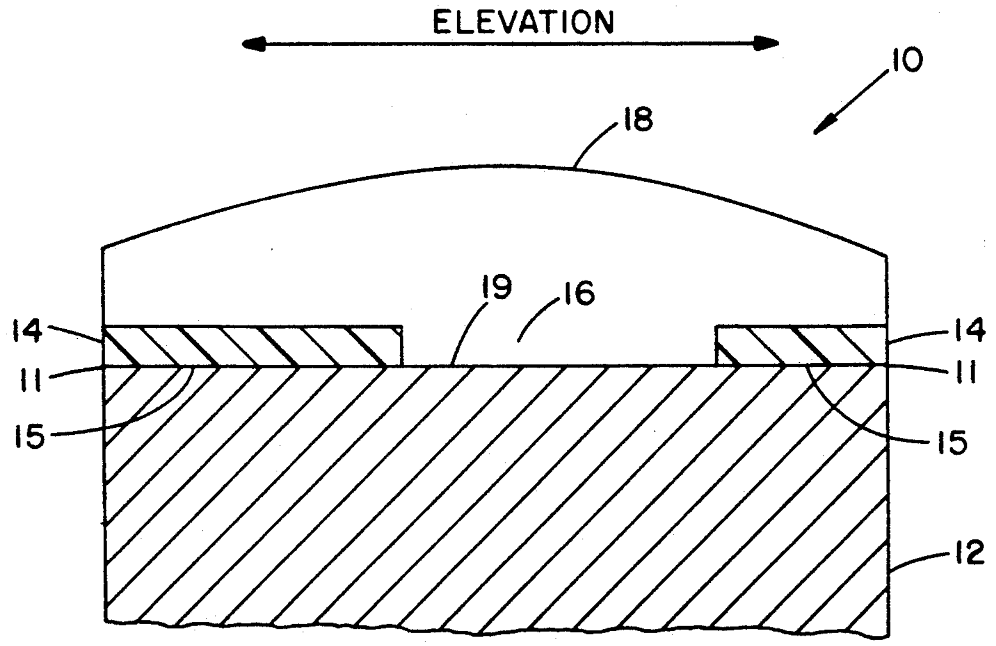
FIG. 1 is a cross-sectional view taken across the lateral axis of the apodized ultrasound transducer featuring a thin sheet blocking layer of this invention.

Referring to FIG. 1, there is shown the cross section of an ultrasound phased array transducer 10 featuring the improved acoustic blocking apodizer of this invention. Transducer 10 is shown cut across the lateral (long) axis, parallel to the elevational (short) axis of the transducer. Transducer 10 includes a piezoelectric stack 12 having a top surface 11. Stack 12 is a typical phased array transducer element stack, which is well known in the art. This stack can, for instance, be a conventional phased array of parallel transducer elements distributed uniformly along the lateral axis, with each element parallel to the elevational axis.

A polymer thin sheet blocking layer 14 is laid on the top surface 11 of transducer stack 12 and functions as the apodizer of this invention. Thin sheet blocking layer 14 is patterned to cover portions 15 of the top surface 11, and leave uncovered voids 16 over other portions 19 of the surface 11. Voids 16 define the active areas and covered portions 15 define the inactive areas of the transducer stack surface. That is, those areas of the stack surface lying directly beneath blocking material 14 are disabled as inactive due to the acoustic blocking properties of the material. Those areas of the transducer surface located directly below voids 16 in the blocking material do not experience the same acoustic blocking effect and therefore remain as the active portion of the transducer surface. An acoustic lens 18 is laid over the surface of the transducer stack 12 and the thin sheet blocking layer 14 to form a laminated transducer structure. Acoustic lens 18 may, for instance, be a poured material such as RTV.

Thin sheet blocking layer 14 is configured from a sheet of thin, acoustically scattering, material capable of substantially blocking sound from going into or out of the top surface of transducer stack 12. In one preferred embodiment, the material is 3-5 mil thick TYVEK polymer, commercially available from DuPont. This material has been found to be excellent as an acoustic blocking material, and has a round trip acoustic transmission rate of about −60 db over the frequency range from 2-7 MHz. Furthermore, acoustic reflection at a TYVEK/water interface is random scattering instead of specular reflection, which makes the material an excellent acoustic blocker. Other material properties that make TYVEK an excellent choice for the thin sheet blocking layer are that the material maintains its shape after patterning, is easy to work with, is bondable, is relatively inert and can withstand the good range of environmental conditions, and does not significantly degrade acoustically with increased moisture absorption.

Other materials having similar acoustic and material properties can also be used as the thin sheet blocking layer of this invention. Generally, the blocking material requires a high trapped air content which acts as an acoustic scattering medium. TYVEK, for instance, is a woven polymer fiber material having a significant quantity of air trapped within the weaving. Foam teflon, for instance, is another material which can act as an acoustic scattering medium. Furthermore, thin film layers which trap air can be deposited directly onto the transducer surface, or some other substrate, to form the blocking layer. Preferably, the material should have an acoustic transmission rate of −40 dB or less.

Thin sheet blocking layer 14 is first patterned to form a cut-out mask of the desired geometrical pattern. This mask is installed onto the front surface of the transducer stack 12 and temporarily held in place with an adhesive. The remainder of the transducer fabrication process is accomplished in a regular manner with the result being a finished transducer having the thin sheet blocking layer 14 laminated onto the transducer face. The blocking layer mask can also be installed in front of the lens, or even embedded inside the lens. Best results are achieved by applying the apodizing layer directly to the transducer face to prevent sound energy trapping problems. However, experimental tests have shown that placement of the blocker in front of the lens is acceptable and does not produce significant trapped sound problems.

The blocking layer 14 may be patterned from the thin sheet material in any of a number of ways. These patterning methods include manual cutting by hand under a microscope, laser trimming, die stamping, or photolithographic/acid etching.

Figure 2:
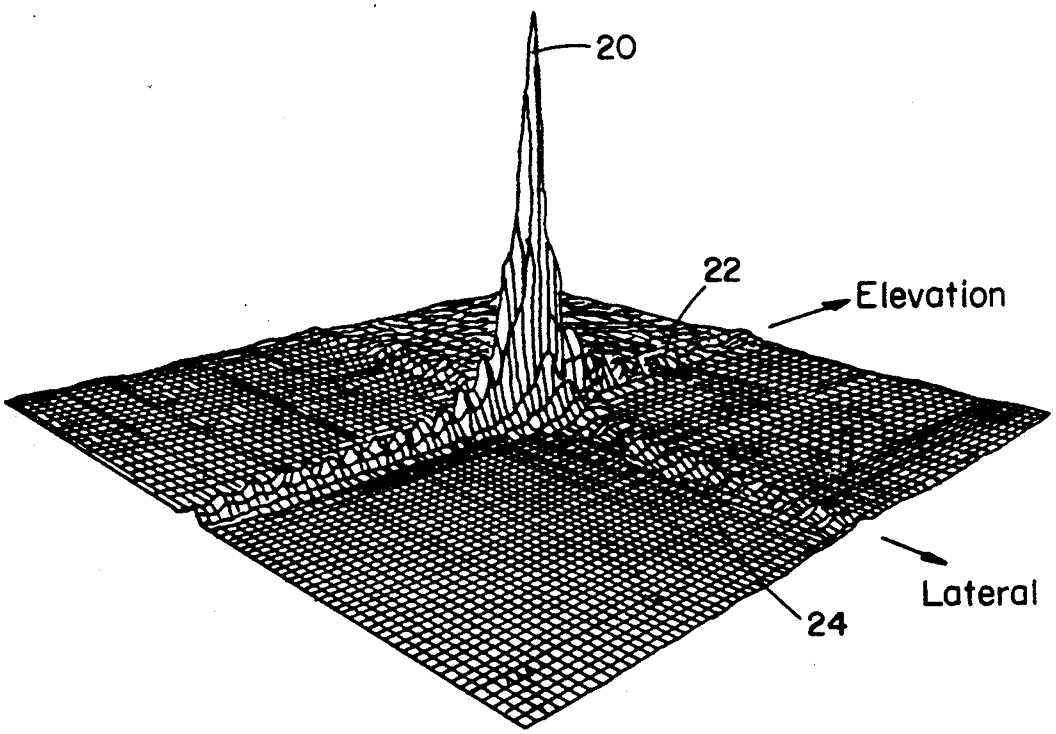
FIG. 2 PRIOR ART
FIG. 2 is a simulated three-dimensional beam plot of a conventional prior art transducer showing substantial side lobe energy along the elevation axis.

Referring to FIG. 2, there is shown a simulated three-dimensional beam plot for a typical prior art phased array transducer producing a beam steered perpendicular to the face of the transducer, and without apodization. This plot shows that the typical characteristics of a phased array transducer without apodization include a narrow, sharply focused main lobe 20, with significant side lobe energy 22 along the elevational axis, and relatively low side lobe energy along the lateral axis of the transducer. It is the significant side lobe energy in the elevational direction 22 which interferes with the quality of the image producible by the main lobe 20. It is an object of this invention to reduce the elevational side lobe energy 22 through aperture windowing, or apodization.

Figure 3:
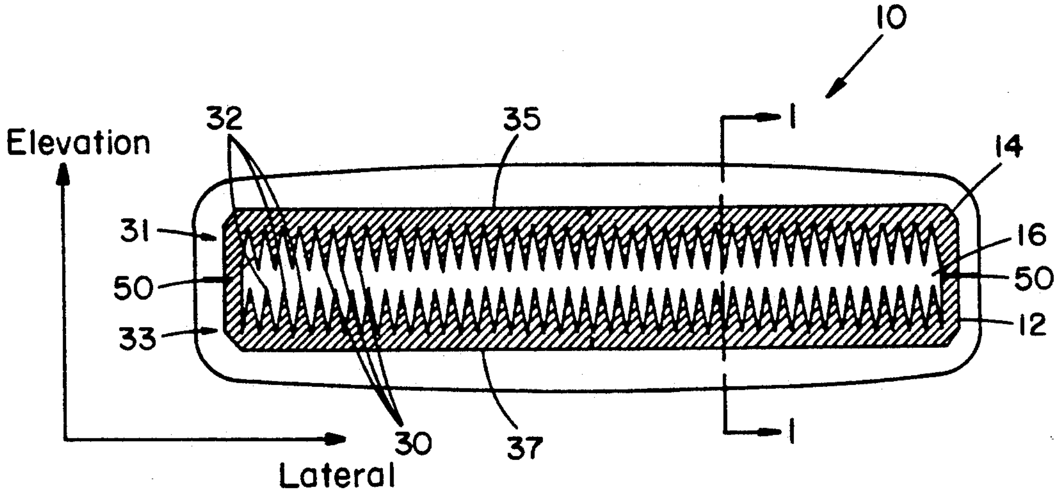
FIG. 3 is a top view of the apodized ultrasound transducer of FIG. 1 showing the uniform anti-symmetric sawtooth blocking pattern for the thin sheet blocking layer of this invention.

Referring to FIG. 3, there is shown a preferred embodiment of the thin sheet blocking layer 14 (FIG. 1) patterned as two rows 31 and 33 of uniformly spaced and shaped sawteeth 30, and 32, respectively. Rows 31 and 33 are disposed along opposite peripheral edges 35 and 37, respectively, of the top surface of transducer stack 12. The base of each tooth is connected to the base of an adjacent tooth along its corresponding peripheral edges to totally block the top surface at each peripheral edge. The teeth 30 of row 31 are anti-symmetric to the teeth 32 of row 33, with both rows of teeth pointing toward the center midline 50 of the transducer. That is, each tooth 30 of row 31 is aligned between two teeth 32 of opposite row 33, and vice versa, to provide a uniform, anti-symmetric pattern.

Teeth 30 of row 31, and teeth 32 of row 33, are uniformly spaced at a pitch equal to about 5λ, where λ equals the wavelength of the transducer elements. The apodization percentage achieved by the thin sheet blocking layer pattern of FIG. 3 is about 80% apodization, where the tip to tip spacing between teeth 30 and 32 represent 20% of the total distance across the transducer face along the elevation direction.

Figure 4:
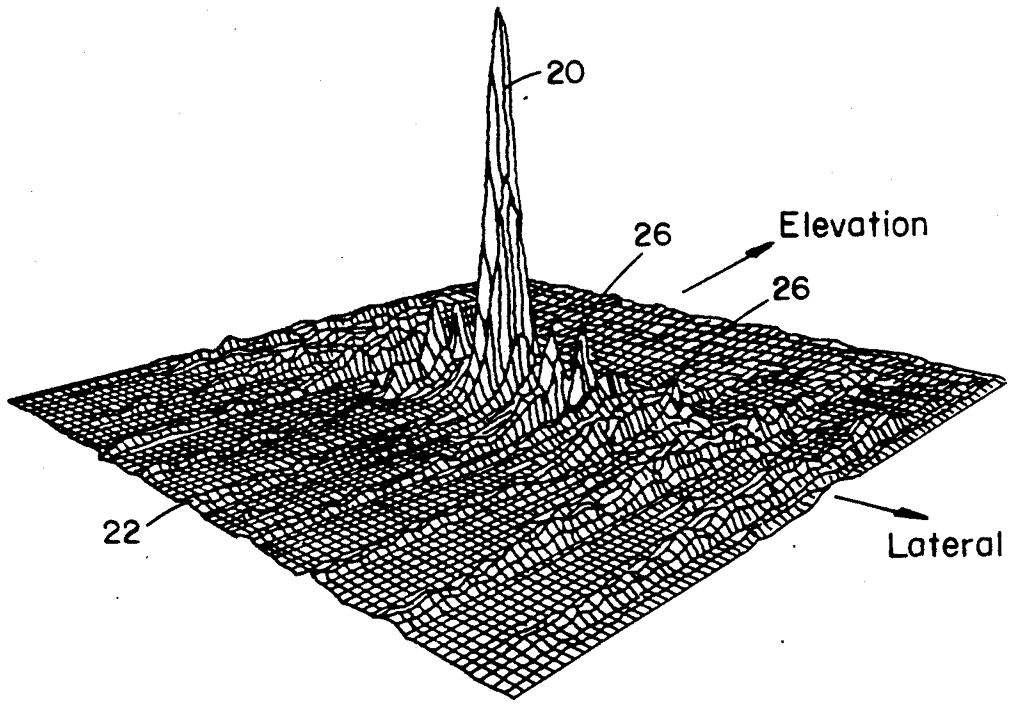
FIG. 4 is a simulated three-dimensional beam plot of the apodized transducer of FIG. 3.

Referring to FIG. 4, there is shown a simulated three-dimensional beam plot taken with a phased array transducer having the thin sheet blocking pattern of FIG. 3. Comparison of the beam plot of FIG. 4 with that of the prior art beam plot of FIG. 2 shows that the main lobe 20 has broadened somewhat resulting in a less sharp focus, which is typical for apodized transducers. There is also a significant reduction of elevational side lobes 22 which are now barely perceptible. There is, however, a significant increase in grating lobes 26, distributed along the lateral axis, which are caused by the uniform, periodic pattern of teeth 30 and 32 of the blocking layer pattern of FIG. 3. These teeth have the effect of modulating the aperture of the transducer to thereby redistribute energy into the periodic grating lobes. One means of eliminating grating lobes 26 as a factor effecting the imaging quality of main lobe 20, is to decrease the tooth pitch of the apodizer blocking pattern of FIG. 3, i.e., move the teeth closer together. Decreasing the tooth pitch effectively moves the grating lobes 26 further away from the main lobe 20, and reduces their number. Preferably, a tooth pitch of approximately ½λ would most likely eliminate the effect of grating lobes on the imaging quality of main lobe 20.

Figure 5:
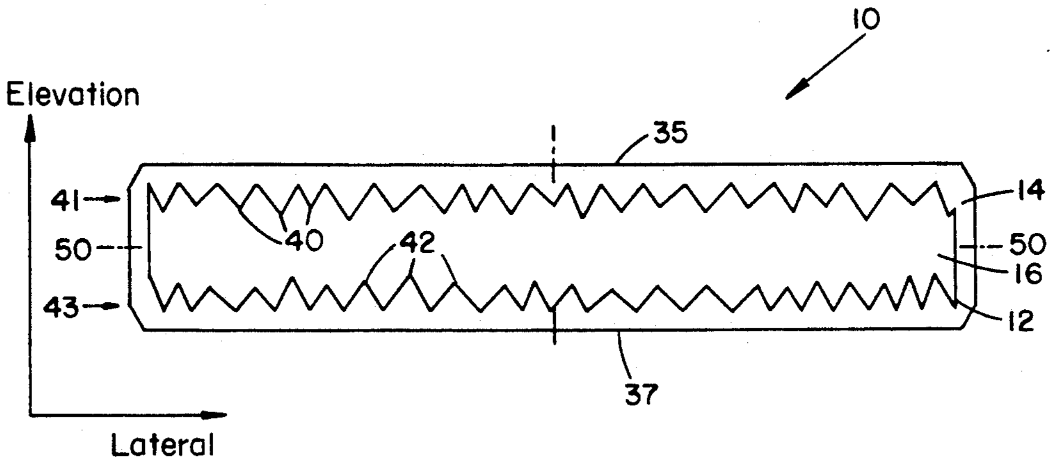
FIG. 5 is a top view of the apodized ultrasound transducer of FIG. 1 showing the pseudo-random sawtooth blocking pattern for the thin sheet blocking layer of this invention.

Referring to FIG. 5, there is another preferred embodiment of a blocking pattern for thin sheet blocking layer 14 of FIG. 1. This blocking layer pattern features a pseudo-random tooth pattern having two rows 41 and 43 of opposing teeth 40 and 42 disposed on opposite peripheral edges 35 and 37, respectively, of the top surface of transducer stack 12. Each of the teeth 40 of row 41, and 42 of row 43, are pseudo-randomly sized and non-periodically spaced. The pseudo-random, non-periodic nature of the teeth provides a high degree of apodization, but without the grating lobes 26 (FIG. 4) produced by the blocking pattern of FIG. 3.

Figure 6:
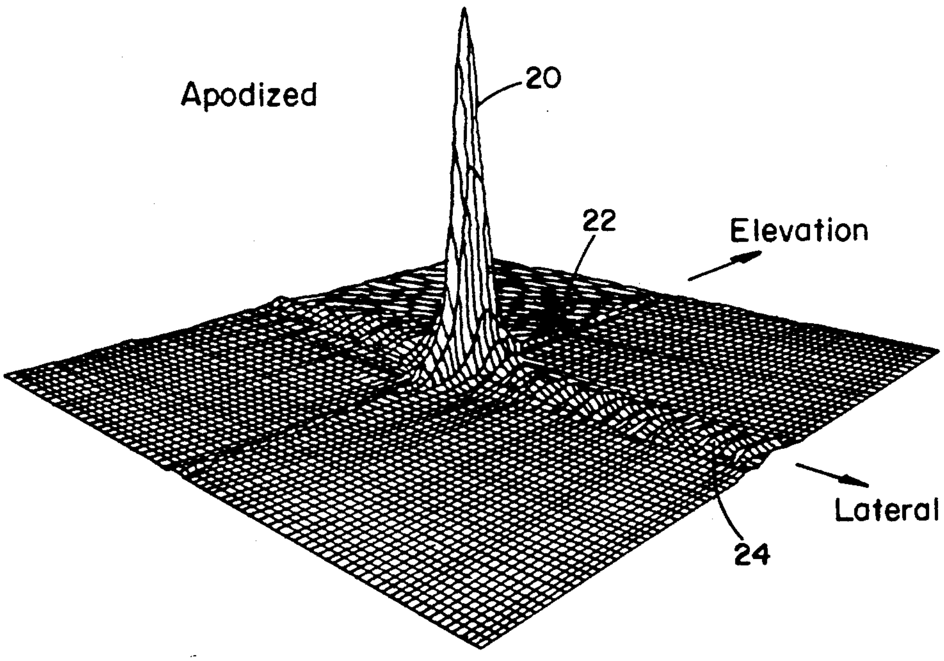
FIG. 6 is a simulated three-dimensional beam plot of the apodized transducer of FIG. 5.

FIG. 6 is a simulated three-dimensional beam plot of a phased array transducer having the apodizer blocking pattern of FIG. 5, confirming the virtual elimination of elevational side lobes 22, and the lack of grating lobes 26 present in FIG. 4. Main lobe 20 is similar to that shown in FIG. 4 for the blocking pattern of FIG. 3. The lateral axis side lobes 24 are similar to those of prior art of FIG. 2. The overall noise floor, however, has increased due to the randomized relocation of energy which would otherwise be present in the grating lobes. That is, randomization of the teeth pattern shown in FIG. 5 causes the energy which would otherwise be present in the grating lobes of FIG. 4 to be redistributed in a more uniform fashion across the entire beam plot, resulting in an increased overall noise floor. However, the increased noise floor has an insignificant effect on the overall imaging quality of the main lobe, when compared to the significant performance improvement caused by elimination of the elevation side lobes without the production of significant grating lobes.

Figure 7A:
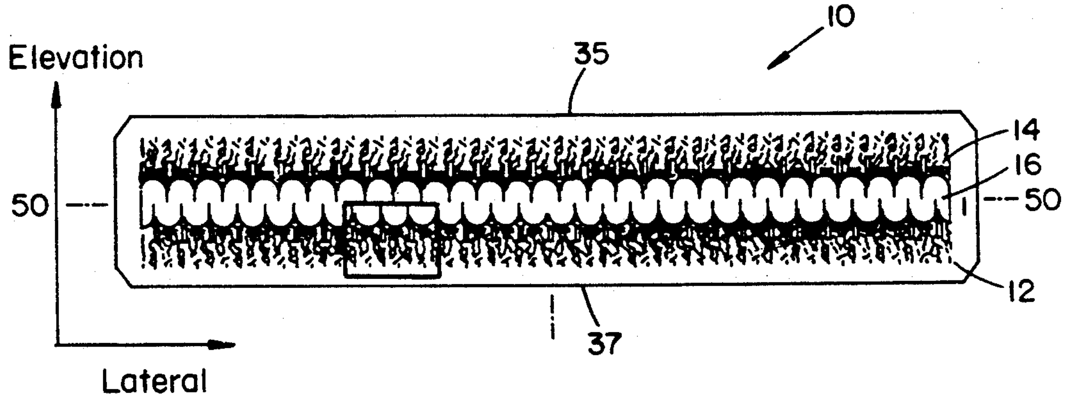
FIGS. 7(*a*)–7(*c*) are top views of the apodized ultrasound transducer of FIG. 1 showing the pseudo-random blocked screen pattern for the thin sheet blocking layer of this invention.
Figure 7B:
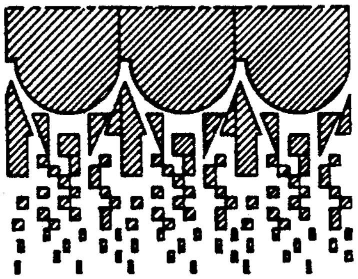
Figure 7C:
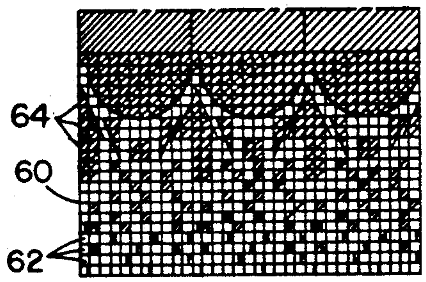

FIGS. 7(*a*) and 7(*b*), show another preferred embodiment of a blocking pattern for the thin sheet blocking layer 14 of FIG. 1. This blocking pattern achieves random blocking of the acoustic energy similar to that of FIG. 5. In this case, the blocking pattern is fashioned as a grid pattern 60 having certain pseudo-randomly selected grids 62 (shown as white squares) remain blocked as shown in detail in FIG. 7(*c*). The remainder of the grids 64 (shown as dark squares) are cut-out to produce voids in the thin sheet layer. The percentage of apodization is dependent on the area of the screen blocked across the elevational direction. That is, the percentage of the transducer face area covered by the blocking material determines the percentage of apodization. Pseudo-randomly blocked grids 62 are distributed in the grid pattern 60 such that holes in the grid pattern are larger at the midline 50 and smaller at the peripheral edges 35 and 37 to produce a windowing effect along the elevation direction. Where the percentage of holes exceeds a certain limit, there may be a need for a regular cut out pattern in the screen.

Figure 8:
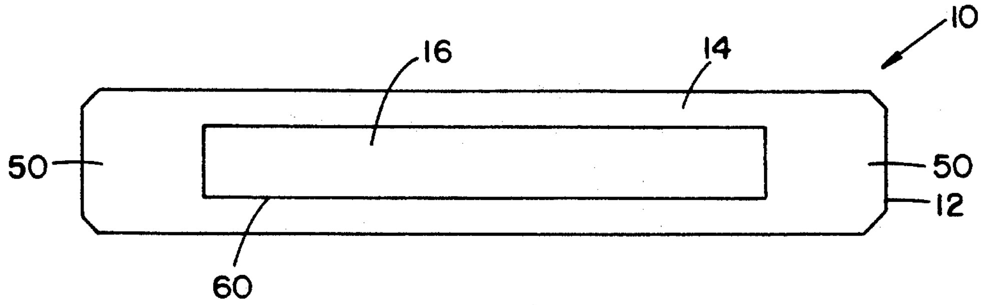
FIG. 8 is a top view of the apodized ultrasound transducer of FIG. 1 showing the rectangular aperture blocking pattern of this invention.

FIG. 8 shows another preferred embodiment of a blocking pattern for the thin sheet blocking layer 14 of FIG. 1. In this case the blocking pattern has a regular rectangular cut-out forming a new aperture 60 for piezoelectric transducer element 12. In this manner the aperture of a transducer can be adjusted by simply changing the dimensions of the cut-out in the thin sheet blocking layer.

Figure 9:
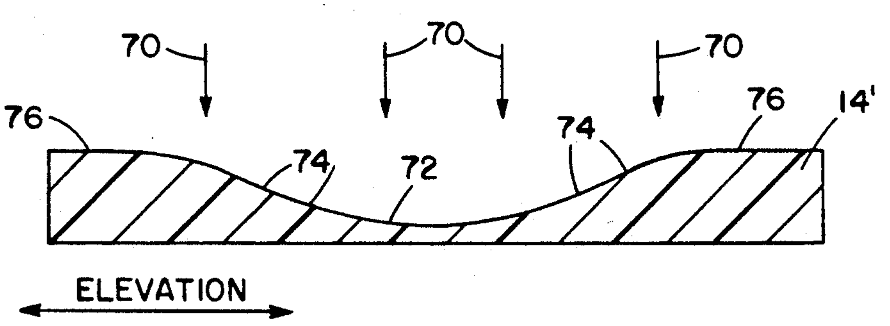
FIG. 9 is a cross-sectional view of a thin sheet blocking layer of this invention processed to have variable attenuation characteristics.

FIG. 9 shows another preferred embodiment of a blocking layer 14′ featuring variable acoustic attenuation properties. Blocking layer 14′ is shown in cross-section along the elevation axis. In this case, an unpatterned sheet of blocking material is physically altered to vary its acoustic absorption properties over its surface area. In this case, for instance, a heat pressing process 70 is applied to a layer of TYVEK material to compress areas 72 of the material, partially compress other areas 74 of the material, and leave uncompressed still other areas 76 of the material. Since TYVEK relies on trapped air for its acoustic absorption properties, the compressed area 72 becomes essentially acoustically transparent. Furthermore, the partially compressed areas 74 retain some degree of acoustic absorption, but are more acoustically transparent than the uncompressed areas 76. Uncompressed areas 76 retain their full acoustic blocking properties. Thus, virtually any variable attenuation apodization pattern can be configured on blocking layer 14′ by selectively compressing certain regions of the blocking layer.

Figure 10:
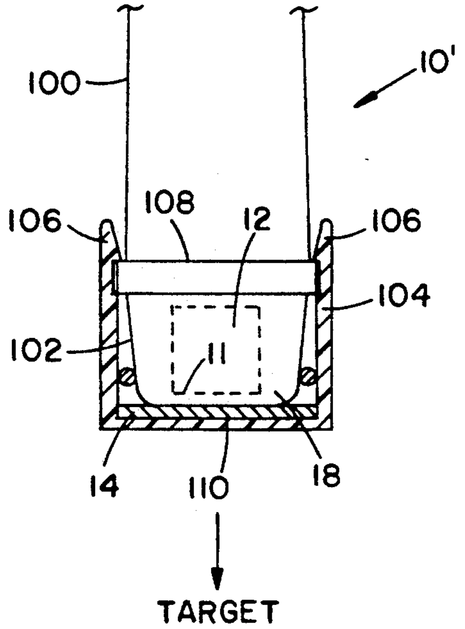
FIG. 10 is a cross-sectional view of an apodization sleeve containing the thin sheet blocking layer of this invention for removably fitting over the end of an ultrasound transducer.

FIG. 10 shows another method of attaching the thin sheet blocking layer 14 of this invention to the front of an ultrasound transducer 10′. An adapter sleeve 104 allows the apodization or aperture characteristics of the ultrasound transducer to be quickly and accurately modified since each sleeve can contain a differently configured blocking layer 14. Ultrasound transducer 10′ has an elongated body portion 100 which functions as a handle, and a head portion 102 which contains the piezoelectric transducer element 12. Lens 18 is typically integrally incorporated into the head portion 102. Adapter sleeve 104 is fashioned to slip over the head portion 102 where it is snapped into place by resilient clips 106 which connect to the edge of a flange 108 encircling the transducer head 102.

Sleeve 104 has the thin sheet blocking layer 14 of this invention attached to the surface of an acoustic window 110 so that the blocking layer is effectively held between the transducer lens 18 and the target. Preferably, the blocking layer is held tightly against the lens, but some gap can also be present. The lens is preferably acoustically coupled to the blocking layer with water or acoustic coupling gel. A rubber o-ring 112 is positioned around the circumference of the transducer head 102 between the head and the interior of the sleeve 104 to help seal the end of the transducer head to the sleeve.

While this invention has been particularly shown and described with reference to preferred embodiments thereof, it will be understood by those skilled in the art that various changes in form and details may be made therein without departing from the spirit and scope of the invention as defined by the appended claims. For instance, although apodization has been described with respect to the elevation direction of an ultrasound transducer, it can also be applied along the lateral direction of the transducer to adjust the beamforming characteristics. Apodization patterns featuring sawteeth have been described, but other patterns featuring sinusoidal or rectangular teeth, or rosettes, can also be used. The transducer element has been described herein as a rectangular phased array, but the thin sheet blocking layer of this invention can be applied to other types of ultrasound transducers, such as single crystal or annular array transducers.

We claim:

1. An ultrasound transducer for imaging a target comprising:

a piezoelectric transducer element having a front surface for emitting an ultrasonic wave toward the target, and for receiving an echo of the emitted ultrasonic wave returned from the target, and ultrasound blocking means comprising a thin sheet of blocking material integral with the transducer for substantially blocking the ultrasonic wave emission from a portion of the front surface area defining an inactive area of the front surface, and for allowing substantial transmission of the ultrasonic wave emission from another portion of the front surface area defining an active are of the front surface.

2. The ultrasound transducer of claim 1, wherein the ultrasound blocking means is patterned for covering the inactive area of the front surface.

3. The ultrasound transducer of claim 2, wherein the blocking material is thin sheet having acoustic blocking attenuation of at least −40 dB at the ultrasonic wave frequency.

4. The ultrasound transducer of claim 3, wherein the thin sheet is TYVEK.

5. The ultrasound transducer of claim 2, wherein the thin sheet of blocking material is attached to the front surface of the transducer element.

6. The ultrasound transducer of claim 2, further comprising:

an acoustic lens integral with the transducer element for focusing the ultrasonic wave emission from the transducer, wherein the thin sheet of blocking material is embedded within the acoustic lens.

7. The ultrasound transducer of claim 2, further comprising a removal by attachable adapter for mounting onto the body of the transducer and for holding the thin sheet of blocking material integral with the transducer element.

8. The ultrasound transducer of claim 2, wherein the thin sheet of blocking material is patterned as a plurality of sawteeth aligned in a first row and pointing toward a midline of the transducer with the bases of adjacent sawteeth connected along an edge corresponding to a first peripheral edge of the front surface of the transducer element, and another plurality of sawteeth aligned in a second row and pointing toward the midline of the transducer with the bases of adjacent sawteeth connected along another edge corresponding to a second peripheral edge opposite the first peripheral edge of the front surface of the transducer element.

9. The ultrasound transducer of claim 8, wherein the sawteeth in each of the first and second rows are uniformly shaped and spaced, and the sawteeth of the first row are positioned anti-symmetric with respect to the sawteeth of the second row.

10. The ultrasound transducer of claim 9, wherein the uniform spacing is less than 10 times the wavelength of the ultrasonic wave.

11. The ultrasonic transducer of claim 8, wherein the sawteeth in each of the first and second row are pseudo-randomly shaped and spaced.

12. The ultrasonic transducer of claim 2, wherein the thin sheet of blocking material is patterned as a grid of pseudo-randomly selected blocking areas.

13. The ultrasound transducer of claim 2, wherein the thin sheet of blocking material is patterned to define the aperture for the transducer element.

14. A phased array ultrasound transducer for imaging a target, comprising:

a phased array piezoelectric transducer element having a front surface for emitting an ultrasonic wave toward the target, and for receiving an echo of the emitted ultrasonic wave returned from the target, the front surface being divided into a plurality of elongated phased array elements distributed along a lateral axis of the transducer front surface with each phased array element substantially parallel to an elevational axis of the transducer front surface, and a patterned thin sheet of acoustic blocking material integral with the transducer for substantially blocking the ultrasonic wave emission from a portion of the front surface area defining an inactive area of the front surface, and for allowing substantial transmission of the ultrasonic wave emission from another portion of the front surface area defining an active area of the front surface.

15. The ultrasound transducer of claim 14, wherein the thin sheet of acoustic blocking material is patterned as a plurality of sawteeth aligned in a first row and pointing toward a midline of the transducer with the bases of adjacent sawteeth connected along an edge corresponding to a first peripheral edge of the front surface substantially parallel to the lateral axis of the transducer element, and another plurality of sawteeth aligned in a second row and pointing toward the midline of the transducer with the bases of adjacent sawteeth connected along another edge corresponding to a second peripheral edge opposite and substantially parallel to the first peripheral edge of the front surface of the transducer element.

16. The ultrasound transducer of claim 15, wherein the sawteeth in each of the first and second rows are uniformly shaped and spaced, and the sawteeth of the first row are positioned anti-symmetric with respect to the sawteeth of the second row.

17. The ultrasonic transducer of claim 16, wherein the sawteeth in each of the first and second row are pseudo-randomly shaped and spaced.

18. The ultrasound transducer of claim 15, wherein the blocking material is a thin sheet having acoustic blocking attenuation of at least −40 dB at the ultrasonic wave frequency.

19. The ultrasound transducer of claim 14 wherein the thin sheet of blocking material is patterned to define the aperture for the transducer element.

20. The ultrasound transducer of claim 14 wherein the thin sheet of blocking material is altered over its surface to provide variable blocking characteristics.

21. An ultrasound transducer for imaging a target comprising:

a piezoelectric transducer element having a front surface for emitting an ultrasonic wave toward the target, and for receiving an echo of the emitted ultrasonic wave returned from the target, and ultrasound blocking means integral with the transducer for substantially blocking the ultrasonic wave emission from a portion of the front surface area defining an inactive area of the front surface, and for allowing substantial transmission of the ultrasonic wave emission from another portion of the front surface area defining an active area of the front surface, wherein the blocking means is patterned as a plurality of sawteeth aligned in a first row and pointing toward a midline of the transducer with the bases of adjacent sawteeth connected along ana edge corresponding to a first peripheral edge of the front surface of the transducer element, and another plurality of sawteeth aligned in a second row and pointing toward the midline of the transducer with the bases of adjacent sawteeth connected along another edge corresponding to a second peripheral edge opposite the first peripheral edge of the front surface of the transducer element.

22. The ultrasound transducer of claim 21, wherein the sawteeth in each of the first and second rows are uniformly shaped and spaced, and the sawteeth of the first row are positioned anti-symmetric with respect to the sawteeth of the second row.

23. The ultrasound transducer of claim 22, wherein the uniform spacing is less than 10 times the wavelength of the ultrasound wave.

24. The ultrasound transducer of claim 21, wherein the sawteeth in each of the first and second row are pseudo-randomly shaped and spaced.

* * * * *